United States Patent [19]

Press et al.

[11] 4,157,444

[45] Jun. 5, 1979

[54] 10-(PIPERAZINYL)THIENO[3,4-b][1,5]BENZOXAZEPINES AND 10-(PIPERAZINYL)THIENO[3,4-b][1,5]BENZOTHIAZEPINES

[75] Inventors: Jeffery B. Press, Bellvale, N.Y.; Sidney R. Safir, River Edge, N.J.

[73] Assignee: American Cyanamid Company, Stamford, Conn.

[21] Appl. No.: 886,233

[22] Filed: Mar. 13, 1978

[51] Int. Cl.$^2$ .................. C07D 498/04; C07D 513/04

[52] U.S. Cl. ................. 544/359; 260/327 B; 260/329 S; 260/332.2 C; 424/250

[58] Field of Search ........................ 544/359

Primary Examiner—Donald G. Daus
Assistant Examiner—Lisa Jones
Attorney, Agent, or Firm—Edward A. Conroy, Jr.

[57] ABSTRACT

This disclosure describes 10-[4-(substituted)-1-piperazinyl]thieno[3,4-b][1,5]benzoxazepines and 10-[4-(substituted-1-piperazinyl]thieno[3,4-b][1,5]benzothiazepines useful as anti-psychotic or neuroleptic agents.

15 Claims, No Drawings

10-(PIPERAZINYL)THIENO[3,4-b][1,5]BENZOXAZEPINES AND 10-(PIPERAZINYL)THIENO[3,4-b][1,5]BENZOTHIAZEPINES

BRIEF SUMMARY OF THE INVENTION

This invention relates to new organic compounds and, more particularly, is concerned with novel 10-[4-(substituted)-1-piperazinyl]thieno[3,4-b][1,5]benzoxazepines and 10-[4-(substituted)-1-piperazinyl]thieno[3,4-b][1,5]benzothiazepines which may be represented by the following structural formula:

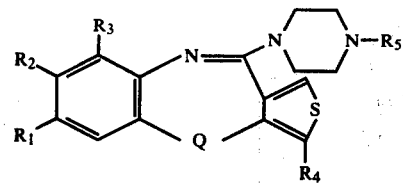

wherein Q is oxy (—O—) or thio (—S—); $R_1$ is hydrogen, lower alkyl or lower alkoxy; $R_2$ is hydrogen, halogen or lower alkyl; $R_3$ is hydrogen or lower alkyl; $R_4$ is hydrogen or halogen; and $R_5$ is lower alkyl or monohydroxy alkyl. Suitable lower alkyl and lower alkoxy groups contemplated by the present invention are those having up to four carbon atoms such as methyl, ethyl, iso-propyl, sec-butyl, methoxy, ethoxy, n-propoxy, isobutoxy, etc. whereas halogen is exemplified by chloro, bromo and iodo. Suitable monohydroxy alkyl groups contemplated by the present invention are those having from two to four carbon toms such as, for example, 1-hydroxyethyl, 1-methyl-2-hydroxyethyl, 2-hydroxypropyl, 3-hydroxypropyl, 2-methyl-3-hydroxypropyl, 1,2-dimethyl-2-hydroxyethyl and 4-hydroxybutyl.

DETAILED DESCRIPTION OF THE INVENTION

The novel compounds of the present invention are obtainable as crystalline materials having characteristic melting points and absorption spectra. They are appreciably soluble in many organic solvents such as lower alkanols, acetone, ethyl acetate, and the like but are generally insoluble in water. These compounds are organic bases and thus are capable of forming acid-addition salts with a variety of organic and inorganic salt-forming reagents. Thus, acid-addition salts, formed by admixture of the organic free base with up to two equivalents of an acid, suitably in a neutral solvent, are formed with such acids as sulfuric, phosphoric, hydrochloric, hydrobromic, sulfamic, citric, maleic, fumaric, tartaric, acetic, benzoic, gluconic, ascorbic, and related acids. The acid-addition of the novel compounds of the present invention are, in general, crystalline solids relatively soluble in water, methanol and ethanol but relatively insoluble in non-polar organic solvents such as diethyl ether, benzene, toluene, and the like. For purposes of this invention, the free bases are equivalent to their non-toxic acid-addition salts.

The novel 10-[4-(substituted)-1-piperazinyl]-thieno[3,4-b][1,5]benzoxazepines (VI) of th- present invention may be readily prepared as set forth in the following reaction scheme:

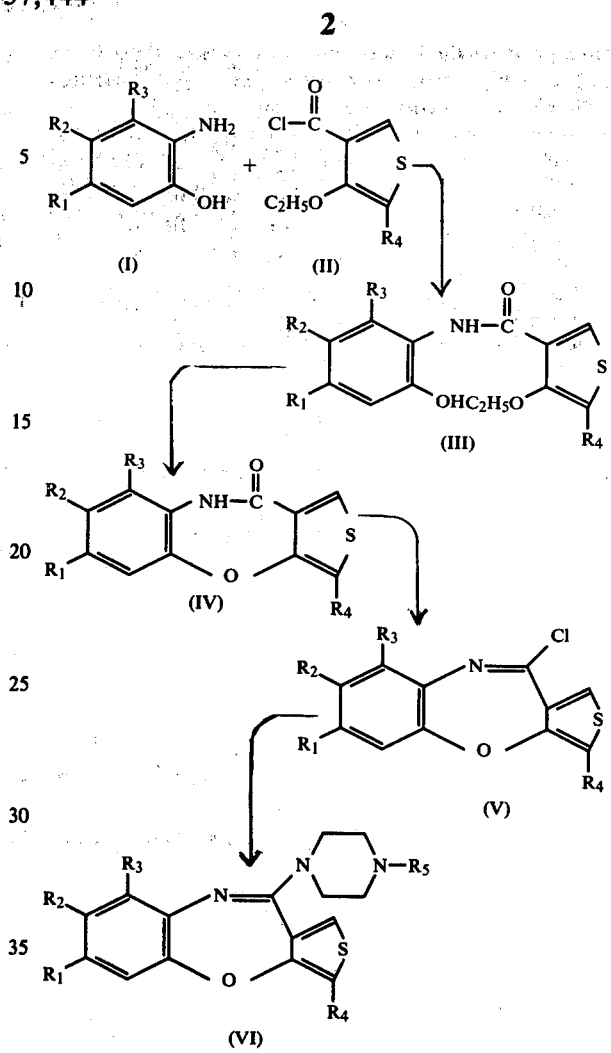

wherein $R_1$, $R_2$, $R_3$, $R_4$ and $R_5$ are as hereinabove defined. In accordance with the above reaction sequence, an appropriately substituted o-aminophenol (I) is acylated with an appropriately substituted 3-thenoyl chloride (II) to provide the corresponding 4-ethoxy-2'-hydroxy-3-thiophenecarboxanilide (III). This acylation reaction is best carried out in an inert solvent such as methylene chloride, benzene, toluene, tetrahydrofuran or dioxane in the presence of an acid acceptor such as triethylamine or soda ash at ambient temperatures for a period of time of 4–12 hours. The 4-ethoxy-2'-hydroxy-3-thiophenecarboxanilide (III) is cyclized by heating in polyphosphoric acid at 100°–150° C. for a period of time of 1–4 hours to provide the corresponding thieno[3,4-b][1,5]benzoxazepin-10(9H)-one (IV). Conversion of the cyclized amide (IV) to the corresponding 10-chlorothieno[3,4-b][1,5]benzoxazepine (V) is accomplished by treating with phosphorus oxychloride or phosphorus pentachloride in an inert solvent such as benzene, toluene or dioxane at the reflux temperature for a period of time of 2–6 hours. Condensation of the 10-chloro derivative (V) with an appropriately substituted piperazine of the formula:

then provides the final product (VI). This condensation is preferably carried out in an inert solvent such as toluene, tetrahydrofuran or dioxane at 100°–150° C. for a period of time of 1–4 hours. In accordance with the above reaction scheme, the isolation and purification of the intermediates and final products is achieved by routine procedures well known to those skilled in the art. Typical compounds of the present invention which may be so prepared are:

3-chloro-6-(n-propyl)-7,8-diethyl-10-[4-(n-propyl)-1-piperazinyl]thieno[3,4-b][1,5]benzoxazepine.
6,8-diisobutyl-7-isopropyl-10-(4-isopropyl-1-piperazinyl)thieno[3,4-b][1,5]benzoxazepine,
3,7-diiodo-6,8-diethyl-10-(4-hydroxymethyl-1-piperazinyl)thieno[3,4-b][1,5]benzoxazepine,
3-bromo-6-ethyl7,8-di(n-propyl)-10-[4-(γ-hydroxypropyl)-1-piperazinyl]thieno[3,4-b][1,5]benzoxazepine,
3,7-dichloro-6,8-dimethyl-10-[4-(ω-hydroxybutyl)-1-piperazinyl]thieno[3,4-b][1,5]benzoxazepine,
6,7,8-tri(n-butyl)-10-[4-(n-butyl)-1-piperazinyl]-thieno[3,4-b][1,5]benzoxazepine,
3-chloro-6,8-diisopropyl-7-ethyl-10-(4-isobutyl-1-piperazinyl)thieno[3,4-b][1,5]benzoxazepine, and
3,7-dibromo-6-(n-butyl)-8-ethyl-10-[4-(sec-butyl)-1-piperazinyl]thieno[3,4-b][1,5]benzoxazepine.

The novel 10-[4-(substituted)-1-piperazinyl]-thieno[3,4-b][1,5]benzothiazepines (XII) of the present invention may be readily prepared as set forth in the following reaction scheme:

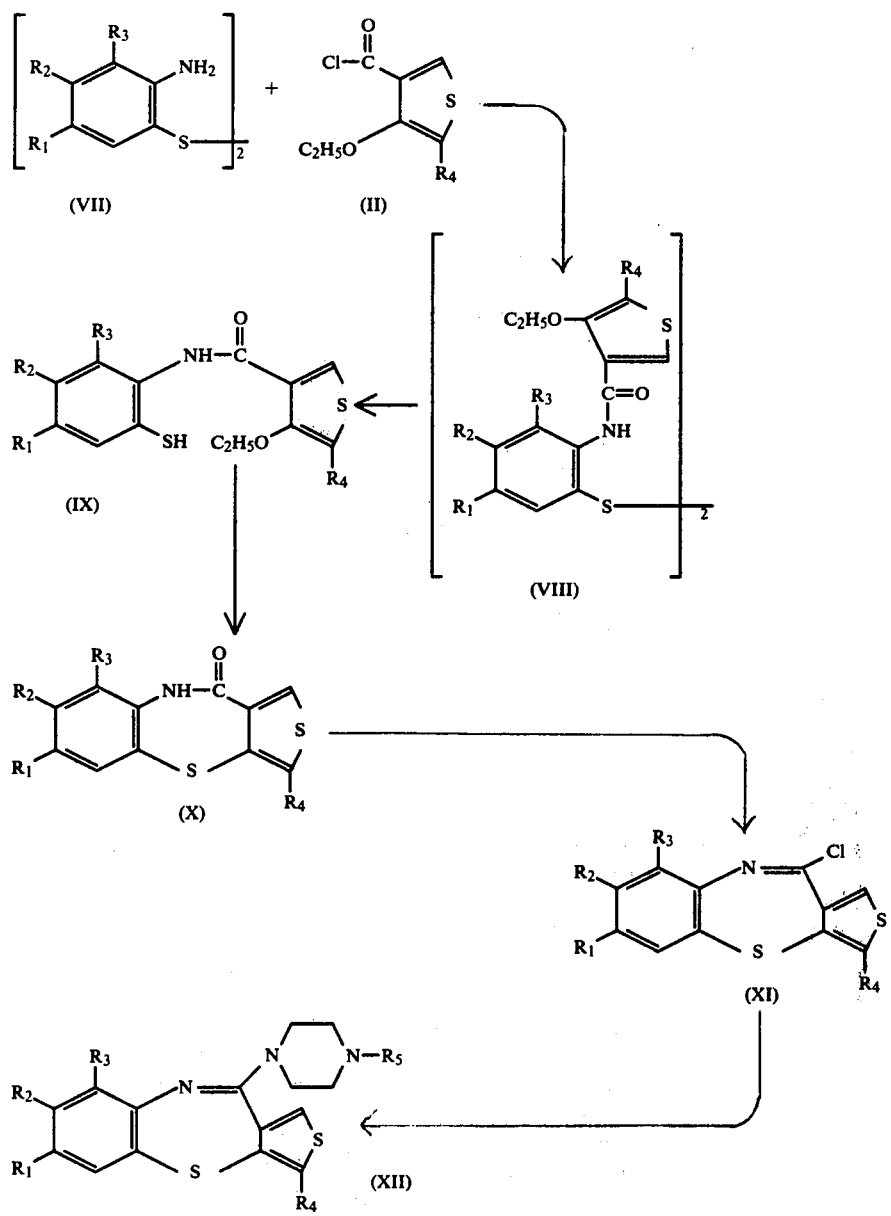

wherein $R_1$, $R_2$, $R_3$, $R_4$ and $R_5$ are as hereinabove defined. In accordance with the above reaction sequence, an appropriately substituted 2,2'-dithiobisaniline (VII) is acylated with an appropriately substituted 3-thenoyl chloride (II) to provide the corresponding o,o'-dithiobis-4-ethoxy-3-thiophenecarboxanilide (VIII). This acylation reaction is best carried out in an inert solvent such as methylene chloride, benzene, toluene, tetrahydrofuran or dioxane in the presence of an acid acceptor such as triethylamine or soda ash at ambient temperatures for a period of time of 4–12 hours. Reduction of the o,o'-dithiobis-4-ethoxy-3-thiophenecarboxanilide (VIII) then provides the corresponding 4-ethoxy-2'-mercapto-3-thiophenecarboxanilide (IX). A variety of chemical reducing agents may be used in this reduction including sodium sulfide, sodium borohydride, sodium dithionite and lithium aluminum hydride. The reduction may also be carried out with active metals such as zinc, tin or iron in acetic acid or mineral acids such as hydrochloric acid. Reduction with metal couples such as the copper-zinc couple, the tin-mercury couple, aluminum amalgam, sodium amalgam or magnesium amalgam may also be used. When aqueous systems are used in the aforementioned chemical reductions, it is at times desirable to utilize a water-miscible organic solvent, particularly when the starting compound is of limited solubility in the reaction mixture. The water-miscible solvent does not alter the course of the reduction but merely provides for more efficient reduction, e.g. a shorter reaction time by providing more intimate contact of the reagents. A large number of such solvents are available for this purpose and include, among others, dimethylformamide, dimethyoxyethane, methanol, ethanol, dioxane, tetrahydrofuran, and the like.

The 4-ethoxy-2'-mercapto-3-thiophenecarboxanilide (IX) is cyclized by heating in polyphosphoric-acid at 100°–150° C. for a period of time of 1–4 hours to provide the corresponding thieno[3,4-b][1,5]benzothiazepin-10(9H)-one (X). Conversion of the cyclized amide (X) to the corresponding 10-chloro-thieno[3,4-b][1,5]benzothiazepine (XI) is accomplished by treating with phosphorus oxychloride or phosphorus pentachloride in an inert solvent such as benzene toluene or dioxane at the reflux temperature for a period of time of 2–6 hours. Condensation of the 10-chloro derivative (XI) with an appropriately substituted piperazine of the formula:

then provides the final product (XII). This then provides the final product (XII). This condensation is preferably carried out in an inert solvent such as toluene, tetrahydrofuran or dioxane at 100°–150° C. for a period of time of 1–4 hours. In accordance with the above reaction scheme, the isolation and purification of the intermediates and final products is achieved by routine procedures well known to those skilled in the art. Typical compounds of the present invention which may be so prepared are:

3-chloro-6-methyl-7,8-di(n-butyl)-10-(4-ethyl-1-piperazinyl)thieno[3,4-b][1,5]-benzothiazepine,
3,7-dibromo-6,8-diethyl-10-(4-hydroxymethyl-1-piperazinyl)thieno[3,4-b][1,5]benzothiazepine,
6,7-di(n-propyl)-8-(sec-butyl)-10-[4-(-hydroxypropyl)-1-piperazinyl]thieno[3,4-b][1,5]benzothiazepine,
3-bromo-6,7-diisopropyl-8-methyl-10-[4-(n-propyl)-1-piperazinyl]thieno[3,4-b][1,5]benzothiazepine,
6-(n-butyl)-7-ethyl-8-isopropyl-10-(4-isopropyl-1-piperazinyl)thieno[3,4-b][1,5]benzothiazepine,
3-iodo-6-isobutyl-7,8-dimethyl-10-[4-(2-hydroxypropyl)-1-piperazinyl]thieno[3,4-b][1,5]benzothiazepine,
3,7-dichloro-6-(sec-butyl)-8-(n-propyl)-10-[4-(-hydroxybutyl)-1-piperazinyl]thieno[3,4-b]benzothiazepine, and
3,7-diiodo-6-methyl-8-isobutyl-10-(4-isobutyl-1-piperazinyl)thieno[3,4-b][1,5]benzothiazepine.

The compounds of the present invention are physiologically active on the central nervous system and show high activity as anti-psychotic or neuroleptic agents. A useful test for anti-psychotic activity consists of measuring the reduction of spontaneous motor activity in animals. The use of reduced motor activity as a measure of neuroleptic activity has been described by Gray et al., Arch. Int. de Pharmaco. et de Therapie 134, 198–215 (1961) and by Kinnard et al., J. Pharmaco and Exp. Ther. 121, 354–361 (1957). The test compounds are administered orally to six to ten individual rats in graded doses. After one hour, a five minute count of motor activity is recorded in an activity counter (Animex ®, Farad Electronics, Sweden). A compound is considered active at a given dose if it causes a 50% reduction of the motor activity count when compared to controls. The results for typical compounds of this invention are given in Table I below.

TABLE I
REDUCED LOCOMOTOR ACTIVITY

| Compound | Dose (mg./kg.) | Result |
| --- | --- | --- |
| 10-(4-Methyl-1-piperazinyl)-thieno[3,4-b][1,5]benzoxazepine fumarate | 1.56 | active |
| 6-Methyl-10-(4-methyl-1-piperazinyl)-thieno[3,4-b][1,5]benzoxazepine fumarate | 50 | active |
| 4-(Thieno[3,4-b][1,5]benzoxazepin-10-yl)-1-piperazineethanol hemifumarate | 6.25 | active |
| 7-Chloro-10-(4-methyl-1-piperazinyl)-thieno[3,4-b][1,5]benzoxazepine hemifumarate | 12.5 | active |
| 4-(6-Methylthieno[4,3-b][1,5]benzoxazepin-10-yl)-1-piperazineethanol fumarate | 50 | active |
| 4-(7-Chlorothieno[4,3-b][1,5]benzoxazepin-10-yl)-1-piperazineethanol fumarate | 25 | active |
| 7-Methyl-10-(4-methyl-1-piperazinyl)-thieno[3,4-b][1,5]benzoxazepine hemifumarate | 12.5 | active |
| 4-(7-Methylthieno[3,4-b][1,5]benzoxazepin-10-yl)-1-piperazineethanol fumarate | 50 | active |
| 10-(4-Ethyl-1-piperazinyl)-thieno[3,4-b][1,5]benzoxazepine fumarate | 3.1 | active |
| 7-Bromo-10-(4-methyl-1-piperazinyl)-thieno[3,4-b][1,5]benzoxazepine hemifumarate | 25 | active |
| 7-Methyl-10-(4-ethyl-1-piperazinyl)-thieno[3,4-b][1,5]benzoxazepine hemifumarate | 50 | active |
| 7-Chloro-10-(4-ethyl-1-piperazinyl)-thieno[3,4-b][1,5]benzoxazepine fumarate | 50 | active |
| 3-Chloro-10-(4-methyl-1-piperazinyl)-thieno[3,4-b][1,5]benzoxazepine fumarate | 50 | active |

Known antipsychotics such as chorpromazine and haloperidol protect grouped mice from the lethal effects of d-amphetamine sulfate. Other types of "tranquilizers" such as Librium ® and Valium ® are ineffective. Groups of 10 mice are treated with the test compounds at a dose of 5 or 10 mg./kg. of body weight. After periodic absorption times the mice are subsequently given intraperitoneal injections of d-amphetamine sulfate at a dose of 15 mg./kg. of body weight. The time of peak effect is established as the absorption time for the respective compounds that protect the greatest percentage of mice from death within 24 hours, with equal to or greater than 50% protection being considered active. The results with typical compounds of this invention appear in Table II below.

TABLE II

PROTECTION VS. d-AMPHETAMINE LETHALITY IN GROUPED MICE

| Compound | Dose (mg./kg.) | Result |
|---|---|---|
| 10-(4-Methyl-1-piperazinyl)-thieno[3,4-b][1,5]benzoxazepine fumarate | 5 | active |
| 4-(Thieno[3,4-b][1,5]benzoxazepin-10-yl)-1-piperazineethanol hemifumarate | 10 | active |
| 7-Chloro-10-(4-methyl-1-piperazinyl)-thieno[3,4-b][1,5]benzoxazepine hemifumarate | 5 | active |
| 4-(7-Chlorothieno[4,3-b][1,5]benzoxazepin-10-yl)-1-piperazineethanol fumarate | 10 | active |
| 7-Methyl-10-(4-methyl-1-piperazinyl)-thieno[3,4-b][1,5]benzoxazepine hemifumarate | 10 | active |
| 4-(7-Methylthieno[3,4-b][1,5]benzoxazepin-10-yl)-1-piperazineethanol fumarate | 10 | active |
| 7-Bromo-10-(4-methyl-1-piperazinyl)-thieno[3,4-b][1,5]benzoxazepine hemifumarate | 10 | active |
| 7-Methyl-10-(4-ethyl-1-piperazinyl)-thieno[3,4-b][1,5]benzoxazepine hemifumarate | 10 | active |
| 7-Chloro-10-(4-ethyl-1-piperazinyl)-thieno[3,4-b][1,5]benzoxazepine fumarate | 10 | active |
| 4-(3-Chlorothieno[3,4-b][1,5]benzoxazepin-10-yl)-1-piperazineethanol fumarate | 10 | active |
| 8-Methyl-10-(4-methyl-1-Piperazinyl)-thieno[3,4-b][1,5]benzoxazepine hemifumarate | 10 | active |
| 3-Chloro-19-(4-methyl-1-piperazinyl)-thieno[3,4-b][1,5]benzoxazepine fumarate | 10 | active |
| 4-(Thieno[3,4-b][1,5]benzothiazepin-10-yl)-1-piperazineethanol | 10 | active |
| 10-(4-Methyl-1-piperazinyl)-thieno[3,4-b][1,5]benzothiazepine fumarate | 10 | active |
| 6-Methoxy-10-(4-methyl-1-piperazinyl)-thieno[3,4-b][1,5]benzoxazepine hemifumarate | 20* | active |

*Intraperitoneal administration.

Some of the novel compounds of the present invention possess anti-depressant activity as established by the inhibition of tetrabenazine induced depression of exploratory behavior in mice. In this test, doses of 25 mg./kg. of body weight of the test compounds are administered intraperitoneally to groups of 5 mice one hour before the administration of tetrabenazine hexamate at an intraperitoneal dose of 30 mg./kg. of body weight which is known to depress markedly the exploratory behavior of normal mice. Thirty minutes later the mice are tested for their exploratory behavior. Individual mice are placed in the center of a horizontal disc (approximately 18 inches in diameter). Inhibition of the depression induced by tetrabenazine is considered present if the mice perform one or more of the following actions within 10 seconds after being placed on the disc:
(1) Animals move to the edge of the disc and look over the edge.
(2) Animals move 180° in place.
(3) Animals display a head movement of 90° immediately followed by a head movement in the opposite direction of at least 45° C.

Administration of the test compounds to additional groups of 5 mice is repeated, the numbers of individual animals showing an anti-depressant response (normal exploratory behavior) is recorded and the results are analyzed by the following scheme (statistically standardized; significant P=less than 0.05).

| | No. Active/No. Tested | |
|---|---|---|
| 1st Stage (5 Animals) | 0/5 | Reject (ineffective anti-depressant) |
| | 1/5–3/5 | Continue to Stage 2 |
| | ≧4/5 | Accept (active anti-depressant) |
| 2nd Stage | 1/5 | Reject |
| 3rd Stage | 2/10–3/10 | Continue to Stage 3 |
| | ≧4/10 | |
| | >4/10 | Reject |
| | >4/15 | Accept |

This method has been described by Greenblatt, E. N. and Osterberg, A. C. in Toxicology and Applied Pharmacology 7, 566–578 (1965). The results of this test, with representative compounds of this invention, are listed in Table III below.

TABLE III

| Compound | Result |
|---|---|
| 4-(3-Chlorothieno[3,4-b][1,5]benzoxazepin-10-yl)-1-piperazine-ethanol, fumarate | Active |
| 3-Chloro-10-(4-methyl-1-piperazinyl)-thieno[3,4-b][1,5]benzoxazepine, fumarate | Active |

The novel compounds of the present invention may be orally administered in compositions such as tablets wherein the principal active ingredient is mixed with conventional tableting ingredients such as corn starch, lactose, sucrose, sorbitol, talc, stearic acid, magnesium stearate, dicalcium phosphate, gums or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac and cetyl alcohol, cellulose acetate and the like. A particularly advantageous enteric coating comprises a styrene maleic acid copolymer together with known materials contributing to the enteric properties of the coating. The liquid forms in which the novel compounds of the present invention may be incorporated for administration include suitably flavored emulsions with edible oils, such as, cottonseed oil, sesame oil, coconut oil, peanut oil, and the like, as well as elixirs and similar pharmaceutical vehicles.

The term dosage form as described herein refers to physically discrete units suitable as unitary dosage for a warm-blooded animal subject, each unit containing a predetermined quantity of active component calculated to produce the desired therapeutic effect in association with the required pharmaceutical diluent, carrier or vehicle. The dosage may vary from one to 70 mg. per kg. of body weight per day preferably in multiple doses. The daily dosage requirement may be from 50 to 2000 mg. The specification for the novel dosage forms are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, segregated multiples of any of the foregoing and other forms as herein described.

The invention will be described in greater detail in conjunction with the following specific examples.

EXAMPLE 1

10-(4-Methyl-1-piperazinyl)-thieno[3,4-b][1,5]-benzoxazepine fumarate

A 320 g. portion of methyl tetrahydro-4-oxo-3-thiophenecarboxylate [Hromatka et al., Monat. Chemie, 104, 1520 (1973)] is dissolved in 650 ml. of isopropenylacetate, 2.0 g. of p-toluenesulfonic acid is added and the mixture is refluxed overnight. The mixture is concentrated, dissolved in 750 ml. of methylene chloride, cooled to −25° C. and 160 ml. of sulfuryl chloride is added over a one hour period. The methylene chloride is distilled off giving 4-acetoxy-3-thiophenecarboxylic acid methyl ester.

A 370 g. portion of the above product is warmed on a steam bath until melted and then added to a mixture of 4.5 liters of absolute ethanol and 11.6 ml. of concentrated sulfuric acid and refluxed for 3 days. The ethanol is removed and the residue is diluted with one liter of ether. The organic layer is washed twice with water, three times with 1 N-sodium hydroxide, twice with saturated saline and dried over sodium sulfate giving 4-ethoxy-3-thiophenecarboxylic acid ethyl ester.

A 200 g. portion of this ethyl ester is dissolved in a mixture of 1700 ml. of ethanol and 170 ml. of water, treated with 150 g. of potassium hydroxide and refluxed for 2 hours. The vollume is reduced to 400 ml., diluted with one liter of water and acidified to pH 2 with 5 N sulfuric acid. The mixture is extracted five times with methylene chloride. The organic layer is treated with charcoal and sodium sulfate, concentrated, diluted with petroleum ether and stored in a cold room overnight. The solid is collected giving 4-ethoxy-3-thiophenecarboxylic acid.

A 30 g. portion of the above acid is treated dropwise over 30 minutes with 35 ml. of thionyl chloride. The mixture is refluxed at 100° C. for 2 hours. The desired product, 4-ethoxy-3-thiophenecarbonylchloride, is recovered by distillation.

A 1.31 g. portion of 4-ethoxy-3-thiophenecarbonyl chloride is dissolved in 10 ml. of dry methylene chloride and then added dropwise to a solution of 0.75 g. of O-aminophenol in 10 ml. of dry methylene chloride with stirring. A 1.0 ml. portion of triethylamine is added and the mixture is then stirred overnight. This mixture is poured into water, stirred for 30 minutes and extracted three times with methylene chloride. The extracts are filtered through diatomaceous earth and then diluted with petroleum ether giving a white solid. This solid is recrystallized from a mixture of 250 ml. of methylene chloride and 250 ml. of petroleum ether giving 4-ethoxy-2'-hydroxy-3-thiophenecarboxanilide as white crystals.

A 2.75 g. portion of the above product is treated with 50 ml. of polyphosphoric acid, ground together to mix and warmed at 120° C. for 1.5 hours. The mixture is cooled, diluted with 200 ml. of water, stirred and then cooled to 5° C. The mixture is filtered, washed twice with water and dried in vacuo at 80° C. This solid is mixed with 400 ml. of hot ethanol and treated twice with charcoal and filtration through diatomaceous earth. The final filtrate is concentrated to 25 ml., cooled to 5° C. and the crystals which form are collected and air dried. These crystals are sublimed at 180°–195° C. giving thieno[3,4-b][1,5]benzoxazepin-10(9H)-one as a pale yellow solid, m.p. 239.5°–241° C.

A 0.44 g. portion of the above product is treated with 0.46 g. of phosphorus pentachloride in 10 ml. of toluene at reflux for 4 hours. The solvent is stripped, the residue is washed with 5 ml. of toluene and the solvent is stripped in vacuo giving 10-chloro-thieno[3,4-b][1,5]benzoxazepine, as a brown-orange oil.

A 3 ml. portion of N-methylpiperazine is added and the mixture is stirred overnight. An additional 2 ml. of N-methylpiperazine is added and the mixture is warmed to 110° C. for one hour. The mixture is cooled, diluted with 40 ml. of water and extracted five times with methylene chloride. The extracts are washed four times with water, dried over sodium sulfate and concentrated to an orange oil. This oil is treated three times with ether and evaporated to a yellow foam.

The above foam (0.16 g.) is dissolved in 2 ml. of ethanol. A 0.062 g. portion of fumaric acid is dissolved in 3 ml. of hot ethanol. The two solutions are combined, warmed for 5 minutes, cooled and stored overnight at 5° C. The mixture is diluted with 2 ml. of ethanol, filtered and the solid is dried in vacuo. The solid is recrystallized from 12 ml. of ethanol with chilling giving the fumarate salt of the desired product as white crystals, m.p. 217°–220° C.

EXAMPLE 2

6-Methyl-10-(4-methyl-1-piperazinyl)-thieno[3,4-b][1,5]benzoxazepine fumarate

An 8.8 g. portion of 4-ethoxy-3-thiophenecarbonyl chloride is treated with 5.68 g. of 6-amino-m-cresol and 6.5 ml. of triethylamine as described in Example 1. The mixture is filtered and the solid is triturated with 30 ml. of water for 3 hours, filtered and the solid is dried in vacuo. This solid is recrystallized from 200 ml. of ethanol, treated with charcoal, filtered through diatomaceous earth and concentrated giving 4-ethoxy-2'- hydroxy-3-thiophenecarboxy-p-toluidide as cream crystals.

A 5.54 g. portion of the above product is treated with 75 g. of polyphosphoric acid as described in Example 1 with final sublimation giving 6-methyl-thieno[3,4-b][1,5]benzoxazepin-10(9H)-one as a pale yellow solid, m.p. 209°–216° C.

A 4.62 g. portion of the above product and 4.60 g. of phosphorus pentachloride are refluxed in 100 ml. of dry toluene for 4 hours. The mixture is concentrated, triturated with toluene and then concentrated in vacuo. The residue, 10-chloro-6-methyl-thieno[3,4-b][1,5]benzoxazepine, is dissolved in 20 ml. of dry toluene, 20 ml. of N-methylpiperazine are added, the mixture is warmed in an oil bath at 110°–115° C. for 2 hours and then allowed to stand overnight. The mixture is concentrated, extracted four times with methylene chloride-water, washed with water, dried over potassium carbonate, concentrated and filtered through magnesol with methylene chloride giving the base as a foam. This base is converted to the fumarate by dissolving 4.60 g. in 15 ml. of absolute ethanol, filtering, rinsing with 15 ml. of absolute ethanol and concentrating the filtrate. This filtrate is combined with a solution of 1.71 g. of fumaric acid in 20 ml. of ethanol, concentrated to 40 ml. and allowed to stand overnight. The mixture is chilled and the precipitate is collected and washed with cold ethanol. This solid is recrystallized from 200 ml. of hot ethanol, treated with charcoal, filtered concentrated and chilled giving the desired fumarate salt as light tan crystals, m.p. 215°–216° C.

EXAMPLE 3

4-(Thieno[3,4-b][1,5]benzoxazepin-10-yl)-1-piperazineethanol hemifumarate

A 7.84 g. portion of thieno[3,4-b][1,5]benzoxazepin-10(9H)-one (Example 1) and 8.0 g. of phosphorus pentachloride in 200 ml. of toluene is refluxed for 4 hours, concentrated, washed with 25 ml. of toluene and concentrated to a residue, comprising 10-chloro-thieno[3,4-b][1,5]benzoxazepine. This residue is dissolved in 25 ml. of toluene, combined with 25 ml. of N-(2-hydroxyethyl)piperazine and heated to 110° C. overnight. This mixture is diluted with 200 ml. of water and 200 ml. of methylene chloride. The organic layer is dried over sodium sulfate to a solid which is dissolved in 400 ml. of 2 N acetic acid, filtered through Celite, basified with concentrated ammonium hydroxide, extracted with methylene chloride and dried over sodium sulfate giving a brown foam. This foam is filtered through Magnesol giving the base compound as a cream foam and is then converted to the hemifumarate as described in Example 1, m.p. 187°–192° C.

EXAMPLE 4

7-Chloro-10-(4-methyl-1-piperazinyl)-thieno[3,4-b][1,5]-benzoxazepine hemifumarate An 8.8 g. portion of 4-ethoxy-3-thiophenecarbonyl chloride is dissolved in 100 ml. of methylene chloride and added dropwise to a mixture of 6.6 g. of 5-chloro-2-hydroxyaniline in 100 ml. of methylene chloride and 6.5 ml. of triethylamine. This mixture is stirred at ambient temperature overnight, concentrated to 100 ml. and filtered. The filtrate is allowed to stand overnight and the precipitate which forms is collected, washed with water and dried in vacuo. This combined precipitate is recrystallized from 200 ml. of ethanol, treated with charcoal, filtered through diatomaceous earth and concentrated giving 5'-chloro-4-ethoxy-2'-hydroxy-3-thiophenecarboxanilide as red brown crystals.

A 5.65 g. portion of the above product is treated with 75 ml. of polyphosphoric acid as described in Example 1, giving 7-chloro-thieno[3,4-b][1,5]benzoxazepin-10(9H)-one as a pale yellow solid, m.p. 263°–265° C.

An 877.3 mg. portion of the above product is treated with 805 mg. of phosphorus pentachloride in 100 ml. of dry toluene as described in Example 1, giving 7,10-dichloro-thieno[3,4-b][1,5]benzoxazepine.

This product is combined with 4.4 ml. of N-methylpiperazine and 5 ml. of toluene and reacted as described in Example 1, giving the base compound as a foam which is reacted with fumaric acid as described in Example 1 to give the crystalline product as the hemifumarate salt, m.p. 180°–182° C.

EXAMPLE 5

4-(6-Methylthieno[3,4-b][1,5]benzoxazepin-10-yl)-1-piperazineethanol fumarate

A 4.62 g. portion of 6-methyl-thieno[3,4-b][1,5]-benzoxazepin-10(9H)-one (Example 2) and 4.58 g. of phosphorus pentachloride in 100 ml. of dry toluene are reacted as described in Example 1 giving 6-methyl-10-chloro-thieno[3,4-b][1,5]benzooxazepine.

This product is dissolved in 20 ml. of dry toluene and reacted with 20 ml. of N-(2-hydroxyethyl)piperazine as described in Example 1, giving the base compound as a foam which is then reacted with fumaric acid as described in Example 1, giving the desired product as the fumarate salt, m.p. 198°–200° C.

EXAMPLE 6

4-(7-Chlorothieno[4,3-b][1,5]benzoxazepin-10-yl)-1-piperazineethanol fumarate

A 1.0 g. portion of 7-chloro-thieno[3,4-b][1,5]benzoxazepin-10(9H)-one (Example 4) and 1.0 g. of phosphorus pentachloride in 25 ml. of toluene are reacted as described in Example 1, giving 7,10-dichloro-thieno[3,4-b][1,5]benzoxazepine.

This product is combined with 4.4 ml. of N-(2-hydroxyethyl)piperazine and 5 ml. of dry toluene and reacted as described in Example 3, giving the base compound as a foam which is then reacted with fumaric acid as described in Example 1, to give the crystalline fumarate salt, m.p. 150°–151° C.

EXAMPLE 7

7-Methyl-10-(4-methyl-1-piperazinyl) thieno[3,4-b][1,5]-benzoxazepine hemifumarate A 10.14 g. portion of 4-ethoxy-3-thiophenecarbonyl chloride is treated with 6.54 g. of 2-amino-p-cresol and 7.4 ml. of triethylamine as described in Example 1. The mixture is filtered and the solid is treated as described in Example 2, giving 4-ethoxy-6'-hydroxy-3-thiophenecarboxy-m-toluidide as cream crystals.

A 5.54 g. portion of the above product is treated with 75 ml. of polyphosphoric acid as described in Example 1, giving 7-methyl-thieno[3,4-b][1,5]benzoxazepin-10(9H)-one as a pale yellow solid, m.p. 209°–213° C.

A 4.62 g. portion of the above product is reacted with 4.60 g. of phosphorus pentachloride in 100 ml. of dry toluene as described in Example 1, giving 7-methyl-10-chloro-thieno[3,4-b][1,5]benzoxazepine which is further reacted with 20 ml. of N-methylpiperazine in 20 ml. of dry toluene, as described in Example 1, giving the base compound as a foam which is further reacted with fumaric acid giving the desired product as the crystalline hemifumarate salt, m.p. 222° C.

EXAMPLE 8

4-(7-Methylthieno[3,4-b][1,5]benzoxazepin-10-yl)-1-piperazineethanol fumarate

7-Methyl-10-chloro-thieno[3,4-b][1,5]benzoxazepine (Example 7) is reacted with 20 ml. of N-(2-hydroxyethyl)-piperazine in 20 ml. of dry toluene as described in Example 1, giving the base compound which is further reacted with fumaric acid, giving the desired product as the fumarate salt, m.p. 178°–180° C.

EXAMPLE 9

4-(7-Bromothieno[3,4-b][1,5]benzoxazepin-10-yl)-1-piperazineethanol hemifumarate A portion of 4-bromophenol is converted to 4-bromo-2-nitrophenol by the method described in Rec. Trav. Chim. 29, 187(1910). A 28 g. portion of 4-bromo-2-nitrophenol is dissolved in 280 ml. of acetone. A 280 ml. portion of water and 112 g. of $Na_2S_2O_4$ are added with stirring. The mixture is refluxed for 2 hours, cooled to room temperature and extracted six times with ether. The ether extracts are washed twice with brine, dried over magnesium sulfate and recrystallized from a mixture of charcoal and 400 ml. of water giving an oil. This oil is redissolved in 600 ml. of water, cooled to 0° C. and filtered giving 5-bromo-2-hydroxyaniline as tan crystals.

A 7.5 g. portion of 4-ethoxy-3-thiophenecarbonyl chloride is dissolved in 50 ml. of methylene chloride and treated with 7.4 g. of 4-bromo-2-hydroxyaniline in 100 ml. of methylene chloride and 5.5 ml. of triethylamine as described in Example 1. The mixture is concentrated to dryness, washed with 50 ml. of water, recrystallized from 900 ml. of ethanol with charcoal treatment and concentrated, giving 5'-bromo-4-ethoxy-2'-hydroxy-3-thiophenecarboxanilide as orange crystals.

A 4.75 g. portion of the above product is treated with 50 ml. of polyphosphoric acid as described in Example 1, giving 7-bromo-thieno[3,4-b][1,5]benzoxazepin-10(9H)-one as a cream colored solid, m.p. 245°–249° C.

A 2.1 g. portion of the above product is reacted with 1.5 g. of phosphorus pentachloride in 40 ml. of dry toluene as described in Example 1, giving 7-bromo-10-chloro-thieno[3,4-b][1,5]benzoxazepine which is further reacted with 15 ml. of N-(2-hydroxyethyl)-piperazine in 15 ml. of dry toluene to give the base compound and, on reaction with fumaric acid, gives the desired product as the hemifumarate, m.p. 150°–152° C.

EXAMPLE 10

10-(4-Ethyl-1-piperazinyl)-thieno[3,4-b][1,5]benzoxazepine fumarate

A 1.08 g. portion of thieno[3,4-b][1,5]benzoxazepin-10(9H)-one and 1.15 g. of phosphorus pentachloride in 22 ml. of dry toluene are reacted as described in Example 1, giving 10-chloro-thieno[3,4-b][1,5]benzoxazepine. To this is added 10 ml. of toluene, 7.2 g. of N-ethylpiperazine and 25 ml. of triethylamine. The mixture is heated overnight at 100° C. and concentrated to dryness. The residue is treated as described in Example 3 providing the base compound as a foam which is converted to the fumarate, m.p. 215°–217° C.

EXAMPLE 11

7-Bromo-10-(4-methyl-1-piperazinyl)-thieno[3,4-b][1,5]benzoxazepine hemifumarate A 2.13 g. portion of 7-bromo-thieno[3,4-b][1,5]benzoxazepin-10(9H)-one (Example 9) and 1.5 g. of phosphorus pentachloride in 40 ml. of dry toluene are reacted as described in Example 9, giving 7-bromo-10-chloro-thieno[3,4-b][1,5]benzoxazepine which is further reacted with N-methylpiperazine in 15 ml. of dry toluene giving the base compound as a foam which is then converted to the hemifumarate, m.p. 196°–197° C.

EXAMPLE 12

4-(3-Chlorothieno[3,4-b][1,5]benzoxazepin-10-yl)-1-piperazineethanol fumarate

An 8.0 g. portion of thieno[3,4-b][1,5]benzoxazepin-10(9H)-one is suspended in 364 ml. of methylene chloride. A 3.27 ml. portion of sulfuryl chloride is added dropwise and the mixture is stirred overnight. The solid is collected and washed with methylene chloride, giving 3-chloro-thieno[3,4-b][1,5]benzoxazepin-10(9H)-one.

A 4.0 g. portion of the above product is reacted with 4.0 g. of phosphorus pentachloride in 103 ml. of dry toluene as described in Example 1, giving 3,10-dichlorothieno [3,4-b]-[1,5]benzoxazepine which is further reacted with 25 ml. of N-methylpiperazine and 25 ml. of dry toluene giving the base compound as a foam which is converted to the fumarate, m.p. 144°–145° C.

EXAMPLE 13

8-Methyl-10-(4-methyl-1-piperazinyl)-thieno[3,4-b][1,5]benzoxazepine hemifumarate A 30.0 g. portion of 3-methyl-2-nitrophenol in 200 ml. of absolute ethanol and 1.0 g. of platinum oxide is hydrogenated to convert to 3-methyl-2-aminophenol.

A 10.86 g. portion of the above product is dissolved in 100 ml. of methylene chloride and 12.3 ml. of triethylamine are added. A 16.76 g. portion of 4-ethoxy-3-thiophenecarbonyl chloride in 100 ml. of methylene chloride is added to the amine solution. The mixture is stirred overnight and then concentrated to dryness. The residue is treated with ethyl acetate and filtered. The filtrate is concentrated to dryness and the residue is triturated with water and filtered giving crystals of 4-ethoxy-6'-hydroxy-3-thiophenecarboxy-o-toluidide.

A 7.0 g. portion of the above product is treated with 114.0 g. of polyphosphoric acid as described in Example 1. The product is sublimed and then recrystallized from methylene chloride-hexane giving 8-methyl-thieno[3,4-b][1,5]benzoxazepin-10(9H) -one, m.p. 194°–195° C.

A 2.90 g. portion of the above product is reacted with 2.61 g. of phosphorus pentachloride and 70 ml. of toluene as described in Example 1, giving 10-chloro-8-methyl-thieno-[3,4-b][1,5]benzoxazepine which in turn is reacted with 15 ml. of N-methylpiperazine in 15 ml. of dry toluene to give the base compound which is then converted to the hemifumarate, m.p. 160°–161° C.

EXAMPLE 14

4-(Thieno[3,4-b][1,5]benzothiazepin-10-yl)-1-piperazineethanol hemifumarate

An 11.45 g. portion of 4-ethoxy-3-thiophenecarbonyl chloride in 100 ml. of methylene chloride is added dropwise to a mixture of 7.44 g. of 2-aminophenyl disulfide and 8.4 ml. of triethylamine in 100 ml. of methylene chloride. The mixture is stirred overnight, concentrated to dryness, treated with 50 ml. of ethyl acetate for 3 hours and filtered. The precipitte is triturated in 50 ml. of water overnight, dried in vacuo and recrystallized from methylene chloride:petroleum ether (20 ml.:200 ml.) giving 2′,2′′′-dithiobis-4-ethoxy-3-thiophenecarboxanilide.

A solution of 0.56 g. of the above product in 50 ml. of methanol and one gram of sodium sulfide nonahydrate are mixed in water and stirred overnight. The mixture is concentrated, neutralized with acetic acid, extracted three times with methylene chloride, washed with water, aqueous sodium bicarbonate and saline, treated with charcoal and then sodium sulfate. The material is then concentrated in vacuo to a yellow oil which solidifies. This solid is recrystallized twice from methylene chloride-petroleum ether at 0° C. and finally from hexane at 0° C. giving 4-ethoxy-2′-mercapto-3-thiophenecarboxanilide.

A 2.0 g. portion of the above product is treated with 50 g. of polyphosphoric acid as described in Example 1, giving thieno[3,4-b][1,5]benzothiazepin-10(9H)-one as yellow solid, m.p. 215°-216° C.

A 1.16 g. portion of the above product and 1.25 g. of phosphorus pentachloride in 30 ml. of dry toluene are refluxed for 4 hours, concentrated, washed with toluene and concentrated to a solid which is 10-chlorothieno[3,4-b][1,5-benzothiazepine.

This product is reacted with N-(2-hydroxyethyl)piperazine giving the base compound as a foam, which is then converted to the hemifumarate, m.p. 189.5°-190° C.

EXAMPLE 15

3-Chloro-10-(4-methyl-1-piperazinyl)-thieno[3,4-b][1,5]benzoxazepine fumarate

A 4.0 g. portion of 3-chloro-thieno[3,4-b][1,5]benzoxazepin-10(9H)-one is converted to 3,10-dichlorothieno[3,4-b][1,5]benzoxazepine as described in Example 12. This compound is then reacted with N-methylpiperazine giving the base compound as a foam which is further converted to the fumarate, m.p. 150°-151° C.

EXAMPLE 16

10-(4-Methyl-1-piperazinyl)-thieno[3,4-b][1,5]benzothiazepine fumarate

10-Chloro-thieno[3,4-b][1,5]benzothiazepine (Example 14) is reacted with N-methylpiperazine in toluene giving the base compound, which is then converted to the fumarate, m.p. 186°-188° C.

EXAMPLE 17

7-Methyl-10-(4-ethyl-1-piperazinyl)-thieno-[3,4-b][1,5]benzoxazepine hemifumarate A 4.62 g. portion of 7-methyl-thieno[3,4-b][1,5]benzoxazepin-10(9H)-one is reacted with 4.60 g. of phosphorus pentachloride in 88 ml. of toluene as described in Example 7, to give 7-methyl-10-chloro-thieno[3,4-b][1,5]benzoxazepine. To this is added 40 ml. of dry toluene, 4.8 g. of N-ethylpiperazine and 10 ml. of triethylamine. The reaction is heated at 100° C. overnight, concentrated to a thick oil and treated as described in Example 3 giving the base compound which is then converted to the hemifumarate, m.p. 208°-209° C.

EXAMPLE 18

7-Chloro-10-(4-ethyl-1-piperazinyl)-thieno[3,4-b][1,5]benzoxazepine fumarate

A 4.0 g. portion of 7-chloro-thieno[3,4-b][1,5]benzoxazepin-10(9H)-one (Example 4) and 4.0 g. of phosphorus pentachloride in 100 ml. of dry toluene are refluxed for 4½ hours concentrated and triturated with toluene, giving 7,10-dichlorothieno[3,4-b][1,5]benzoxazepine.

This product is then reacted with 3.8 g. of N-ethylpiperazine in 40 ml. of toluene to give the base compound, which is then converted to the fumarate, m.p. 183°-185° C.

EXAMPLE 19

4-(3-Chlorothieno[3,4-b][1,5]benzoxazepin-10-yl)-1-piperazineethanol, fumarate (salt)

A 4.0 g portion of 3-chlorothieno[3,4-b][1,5]benzoxazepin-10(9H)-one (Example 12) and 4.0 g of phosphorus pentachloride in 103 ml of dry toluene is refluxed for 4½ hours. The reaction mixture is concentrated, then is triturated with toluene to give 3,10-dichlorothieno[3,4-b][1,5]benzoxazepine. A 25 ml amount of dry N-(2-hydroxyethyl)-piperazine and 25 ml of dry toluene is added to the product above and the mixture is heated at 120° C. for 16 hours. The reaction mixture is concentrated to a thick oil, the oil is dissolved in hot 2 N aqueous acetic acid, treated with activated charcoal and filtered through diatomaceous earth. The filtrate is cooled and precipitated with concentrated ammonium hydroxide. The precipitate is collected and extracted into methylene chloride, the organic solution is dried over anhydrous sodium sulfate and eluted through magnesium silicate with 2.5 liters of methylene chloride followed by one liter of 1:1 ethyl acetate:methylene chloride. The combined organic solvents are evaporated to yield 2.0 g of 4-(3-chlorothieno[3,4-b][1,5]-benzoxazepin-10-yl)-1-piperazineethanol.

The above product (2.0 g) is dissolved in a minimum amount of hot ethanol, treated with activated charcoal and filtered, then 638 mg of fumaric acid in 10 ml of hot ethanol is filtered into the above solution. The mixture is chilled to give the fumarate salt of the desired product, m.p. 145°-146° C.

EXAMPLE 20

3-Chloro-10-(4-methyl-1-piperazinyl)thieno[3,4-b][1,5]benzoxazepine, fumarate

A 4.0 g portion of 3-chloro-thieno[3,4-b][1,5]benzoxazepin-10(9H)-one (prepared in Example 12) and 4.0 g of phosorus pentachloride in 103 ml of dry toluene is refluxed for ½ hours. The reaction mixture is concentrated, then is triturated with toluene to give 3,10-dichlorothieno[3,4-b][1,5]benzoxazepine. A 20 ml amount of dry N-methylpiperazine and 30 ml of dry toluene is added to the product above and the mixture is heated at 120° C. for 16 hours. The reaction mixture is concentrated to a thick oil, the oil is dissolved in hot 2 N aqueous acetic acid, treated with activated charcoal and filtered through diatomaceous earth. The filtrate is cooled and precipitated with concentrated ammonium hydroxide. The precipitate is collected and extracted into methylene chloride, the organic solution is dried over anhydrous sodium sulfate and eluted through magnesium silicate with 2 liters of methylene chloride followed by 1.5 liters of 1:1 ethyl acetate:methylene chloride. The elutates are evaporated and the products obtained are recrystallized from hexane and combined to yield 3.83 g of 3-chloro-10-(4-methyl-1-piperazinyl)-thieno[3,4-b][1,5]benzoxazepine.

A 3.45 g portion of the above product is dissolved in a minimum amount of hot ethanol and is filtered. The filtrate is concentrated to 50 ml, then 1.33 g of fumaric acid in 15 ml of hot ethanol is filtered into the above solution. The resulting product is collected and dried to give the product of the Example, m.p. 170°–172° C.

EXAMPLE 21

6-Methoxy-10-(4-methyl-1-piperazinyl)thieno[3,4-b][1,5]benzoxazepine, hemifumarate A 49.1 g portion of 3-methoxyphenol is converted to 2-nitro-5-methoxyphenol by the method of Agr. Biol. Chem., 40(12), 2413–2416 (1976) and Agr. Biol. Chem., 39(3), 683–685 (1975) to yield 17.04 g of product as yellow needles.

A 16.45 g portion of the above product is converted to 2-amino-5-methoxyphenol according to Agr. Biol. Chem., 39(3), 683–685 (1975) to yield 11.68 g of product. A 10.62 g portion of the preceding product is dissolved in 125 ml of methylene chloride. A 12.1 ml portion of triethylamine is added and the mixture is stirred. To this mixture is added dropwise 61.5 ml of a solution of 26.72 g of 4-ethoxy-3-thiophenecarbonyl chloride (prepared in Example 1) in 100 ml of methylene chloride. An additional 125 ml of methylene chloride is added and the mixture is stirred overnight. The precipitate is collected, air dried and triturated with water to yield 13.68 g of 4-ethoxy-2'-hydroxy-3-thiophenecarbox-4'-anisidide. A 500 mg portion of the above product is treated with 10.0 g of polyphosphoric acid, ground together to mix and warmed at 110°–115° C. in an oil bath for 80 minutes. The mixture is allowed to cool, then is poured into ice-water. The product is collected and dried, then is extracted with methanol in a soxhlet apparatus for 16 hours. The solvent is evaporated to yield 240 mg of residue. The residue is dissolved in 100 ml of hot methylene chloride, the solution is treated with activated charcoal and filtered. The filtrate is concentrated to 20 ml, chilled and filtered to collect 170 mg of product. A 54.5 mg portion of this material is sublimed at 188° C. to yield 431. mg of 6-methoxy-thieno[3,4-b][1,5]benzoxazepin-10(9H)-one.

A 1.31 g portion of the preceding product (prepared as described above) and 1.09 g of phosphorus pentachloride in 27 ml of dry toluene is refluxed for 4½ hours. The reaction mixture is concentrated then is triturated twice with toluene to give 10-chloro-6-methoxy-thieno[3,4-b][1,5]benzoxazepine. A 15 ml amount of dry N-methylpiperazine and 15 ml of dry toluene is added to the product above and the mixture is heated at 120° C. for 16 hours. The reaction mixture is concentrated to a thick oil, the oil is dissolved in hot 2 N aqueous acetic acid, treated with activated charcoal and filtered through diatomaceous earth. The filtrate is cooled and precipitated with concentrated ammonium hydroxide. The product is collected and the filtrate is extracted with methylene chloride to provide additional product. The combined product is dissolved in methylene chloride and filtered through magnesium silicate. The filtrate is evaporated to provide 1.0 g of the base, 6-methoxy-10-(4-methyl-1-piperazinyl)thieno[3,4-b][1,5]benzoxazepine.

The above base product (1.0 g) is dissolved in a minimum amount of hot ethanol, treated with activated charcoal, filtered and rinsed, then 352 mg of fumaric acid in a minimum of hot ethanol is filtered into the above filtrate. The solution is concentrated and cooled and the precipitate is collected. The solid is recrystallized from hot ethanol, concentrated and chilled to give the product of the Example, m.p. 188°–189° C.

EXAMPLE 22

7-Chloro-10-(4-methyl-1-piperazinyl)-thieno[3,4-b][1,5]benzothiazepine fumarate

A 6.60 g portion of 4-ethoxy-3-thiophenecarbonyl chloride in 50 ml. of methylene chloride is added dropwise to a solution of 5.48 g of 2,2'-(dithio)bis[5-chloroaniline] and 3.54 g. of triethylamine in 100 ml of methylene chloride as in Example 14. After filtration through magnesium silicate, the filtrate was concentrated to dryness and the residue was recrystallized from methylene chloride:petroleum ether to give 2',2'''-(dithio)-bis[5'-chloro-4-ethoxy-3-thiophanecarboxanilide] as yellow crystals, m.p. 179°–181° C.

A 3.55 g portion of the above product in 75 ml ethanol was treated with 0.47 gr. of sodium borohydride and refluxed overnight. The solvent was removed by distillation and the residue was treated with 25 gr. of polyphosphoric acid as described in Example 1 to give 7-chlorothieno[3,4-b][1,5]benzothiazepin-10(9H)-one as a cream solid, m.p. 267°–269° C.

A 0.50 gr. portion of the above product and 0.52 g. of phosphorus pentachloride in 20 ml. of dry toluene are refluxed for 4 hours, concentrated, washed with toluene and concentrated to give 7,10-dichlorothieno[3,4-b][1,5]benzothiazepine as a foam.

This product is reacted with N-methylpiperazine giving the base compound as a yellow foam which is further converted to the fumarate, m.p. 234°–235° C. as a cream solid.

EXAMPLE 23

6,7-Dimethyl-10-(4-methyl-1-piperazinyl)thieno[3,4-b][1,5]benzothiazepine fumarate A solution of 44.5 g of 2-amino-5,6-dimethylbenzothiazole and 160 g of potassium hydroxide in 320 ml of water was refluxed 16 hr. and filtered. The filtrate was neutralized with 50% aqueous acetic acid and cooled to 10° C. The precipitate was collected by filtration and recrystallized from methanol:water to give 6,6'-(dithio)-di-3,4-xylidene as yellow crystals, m.p. 139°–140° C.

A 164 g. portion of the above product in 100 ml. of methylene chloride containing 11.1 g of triethylamine was treated with 20.54 g of 4-ethoxy-3-thiophenecarbonyl chloride in methylene chloride as in Example 14. The crude product is recrystallized from methylene chloride:petroleum ether to give 6'6''-(dithio)bis[4-ethoxy-3-thiophene-3',4'-xylidide] as yellow crystals, m.p. 206°–208° C.

A 12.2 portion of the above product was treated with 1.90 g. of sodium borohydride as in Example 25. The mixture as cooled to 0°, filtered and the filtrate was concentrated invacuo to give a yellow oil. The yellow oil was treated with 75 g of polyphosphoric acid as described in Example 1 to give 6,7-dimethylthieno[3,4-b][1,5]benzothiazepin-10(9H)-one as white crystals, m.p. 264°–265° C.

A 0.58 g. portion of the above product and 0.67 g. of phosphorus pentachloride in 20 ml. of dry toluene were reacted as in Example 25 to give 10-chloro-6,7-dimethylthieno[3,4-b][1,5]-benzothiazepine as a foam.

The above product is reacted with N-methylpiperazine giving 6,7-dimethyl-10-(4-methyl-1-piperazinyl/-thieno[3,4-b][1,5]benzothiazepine as a yellow foam which is converted to the fumarate as a cream solid, m.p. 205°–207° C.

EXAMPLE 24

3-Chloro-10(4-methyl-1-piperazinyl)-thieno[3,4-b][1,5]benzothiazepine fumarate

A suspension of 1.16 g. of thieno[3,4-b][1,5]-benzothiazepin-10(9H)-one in 20 ml. of methylene chloride was treated with 0.81 g of sulfuryl chloride as in Example 12 to give 3-chlorothieno[3,4-b][1,5]benzothiazepin-10(9H)-one as a white crystal, m.p. 287°–288° C.

A 1.09 g. portion of the above product and 0.95 g. of phosphorus pentachloride in 40 ml of dry toluene was refluxed for 4 hours, concentrated, washed with toluene and concentrated to give 3,10-dichlorothieno[3,4-b][1,5]-benzothiazepine as a yellow foam.

This product is reacted with N-methylpiperazine giving the base compound which was cowerted with fumaric acid to 3-chloro-10*4-methyl-1-piperazinyl)-thieno[3,4-b][1,5]benzothiazepine fumarate as yellow crystals, m.p. 163°–165° C.

We claim:

1. A compound selected from the group consisting of those of the formula:

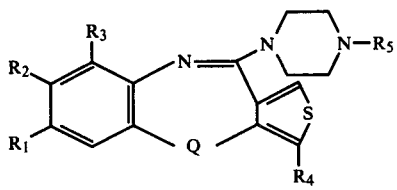

wherein Q is divalent oxygen or divalent sulfur; $R_1$ is selected from the group consisting of hydrogen, alkyl having from one to four carbon atoms and alkoxy having from one to four carbon atoms; $R_2$ is selected from the group consisting of hydrogen, chloro, bromo, iodo and alkyl having from one to four carbon atoms; $R_3$ is selected from the group consisting of hydrogen and alkyl having from one to four carbon atoms; $R_4$ is selected from the group consisting of hydrogen, chloro, bromo and iodo; $R_5$ is selected from the group consisting of alkyl having from one to four carbon atoms and monohydroxy alkyl having from two to four carbon atoms; and the pharmacologically acceptable acid-addition salts thereof.

2. The compound according to claim 1 wherein Q is oxy, $R_5$ is methyl, and $R_1$, $R_2$, $R_3$ and $R_4$ are hydrogen; 10-(4-methyl-1-piperazinyl)thieno[3,4-b][1,5]benzoxazepine.

3. The compound according to claim 1 wherein Q is oxy, $R_2$ is chloro, $R_5$ is methyl, and $R_1$, $R_3$ and $R_4$ are hydrogen; 7-chloro-10-(4-methyl-1-piperazinyl)-thieno[3,4-b][1,5]benzoxazepine.

4. The compound according to claim 1 wherein Q is oxy, $R_5$ is 2-hydroxyethyl, and $R_1$, $R_2$, $R_3$ and $R_4$ are hydrogen; 4-(thieno[3,4-b][1,5]benzoxazepin-10-yl)-1-piperazineethanol.

5. The compound according to claim 1 wherein Q is oxy, $R_2$ and $R_5$ are methyl, and $R_1$, $R_3$ and $R_4$ are hydrogen; 7-methyl-10(4-methyl-1-piperazinyl)thieno[3,4-b][1,5]benzoxazepine.

6. The compound according to claim 1 wherein Q is oxy, $R_2$ is bromo, $R_5$ is methyl, and $R_1$, $R_3$ and $R_4$ are hydrogen; 7-bromo-10-(4-methyl-1-piperazinyl)-thieno[3,4-b][1,5]benzoxazepine.

7. The compound according to claim 1 wherein Q is oxy; $R_4$ is chloro, $R_5$ is methyl, and $R_1$, $R_2$ and $R_3$ are hydrogen; 3-chloro-10-(4-methyl-1-piperazinyl)-thieno[3,4-b][1,5]benzoxazepine.

8. The compound according to claim 1 wherein Q is oxy, $R_2$ is chloro, $R_5$ is 2-hydroxyethyl, and $R_1$, $R_3$ and $R_4$ are hydrogen; 4-(7-chlorothieno[3,4-b][1,5]benzoxazepin-10-yl)-1-piperazineethanol.

9. The compound according to claim 1 wherein Q is thio, $R_5$ is methyl, and $R_1$, $R_2$, $R_3$ and $R_4$ are hydrogen; 10-(4-methyl-1-piperazinyl)thieno[3,4-b][1,5]benzothiazepine.

10. The compound according to claim 1 wherein Q is thio, $R_5$ is 2-hydroxyethyl, and $R_1$, $R_2$, $R_3$ and $R_4$ are hydrogen; 4-(thieno[3,4-b][1,5]benzothiazepin-10-yl)-1-piperazineethanol.

11. The compound according to claim 1 wherein Q is thio, $R_4$ is chloro, $R_5$ is methyl, and $R_1$, $R_2$ and $R_3$ are hydrogen; 3-chloro-10-(4-methyl-1-piperazinyl)-thieno[3,4-b][1,5]-benzothiazepine.

12. The compound according to claim 1 wherein Q is thio, $R_2$ is chloro, $R_5$ is methyl, and $R_1$, $R_3$ and $R_4$ are hydrogen; 7-chloro-10-(4-methyl-1-piperazinyl)-thieno[3,4-b][1,5]benzothiazepine.

13. The compound according to claim 1 wherein Q is oxy, $R_3$ and $R_5$ are methyl, and $R_1$, $R_2$ and $R_4$ are hydrogen; 8-methyl-10-(4-methyl-1-piperazinyl)thieno[3,4-b][1,5]benzoxazepine.

14. The compound according to claim 1 wherein Q is oxy, $R_5$ is ethyl, and $R_1$, $R_2$, $R_3$ and $R_4$ are hydrogen; 10-(4-ethyl-1-piperazinyl)thieno[3,4-b][1,5]benzoxazepine.

15. The compound according to claim 1 wherein Q is oxy, $R_1$ is methoxy, $R_5$ is methyl, and $R_2$, $R_3$ and $R_4$ are hydrogen; 6-methoxy-10-(4-methyl-1-piperazinyl)-thieno[3,4b-][1,5]-benzoxazepine.

* * * * *